United States Patent [19]

Levine et al.

[11] Patent Number: 5,128,318
[45] Date of Patent: Jul. 7, 1992

[54] RECONSTITUTED HDL PARTICLES AND USES THEREOF

[75] Inventors: Daniel M. Levine, New York; Sanford R. Simon, Selden; Bruce R. Gordon, New York; Thomas S. Parker, Brooklyn; Stuart D. Saal, New York, all of N.Y.; Albert L. Rubin, Englewood, N.J.

[73] Assignee: The Rogosin Institute, New York, N.Y.

[21] Appl. No.: 263,543

[22] Filed: Oct. 27, 1988

Related U.S. Application Data

[62] Division of Ser. No. 52,489, May 20, 1987, abandoned.

[51] Int. Cl.$^5$ .............................................. A61K 37/02
[52] U.S. Cl. ......................................... 514/2; 424/450; 436/829; 514/21
[58] Field of Search ............... 424/406, 450, 94.3; 430/829; 514/2.12, 21; 530/380; 604/5, 6

[56] References Cited

U.S. PATENT DOCUMENTS 4,499,184  2/1985  Goodhue ............................ 436/71
4,789,545  12/1988  Woods et al. ...................... 424/89
4,943,527  7/1990  Protter et al. ...................... 435/72

FOREIGN PATENT DOCUMENTS 9345  12/1988  World Int. Prop. O. .......... 530/359

OTHER PUBLICATIONS

Zinsser Microbiology, 19th ed. Joklik et al, eds. Appleton & Lange, 1988, p. 335.
Raetz, "Biochemistry of Endotoxins," *Annu. Rev. Biochem.* 1990, vol. 59, pp. 129-130.
Malmendier et al., "In vivo metabolism of human apoprotein A-I-phospholipid complexes, Comparison with human high density lipoprotein-apoprotein A-I metabolism," *Clinica Chimica Acta*, vol. 131, No. 3 (1983), pp. 200-211.
Segrest et al, *Methods in Enzymology*, Academic Press 1986, vol. 128, pp. 3-41, 223-246, 554-582.
Williams et al, "Uptake of endogenous cholesterol by a synthetic lipoprotein," *Biochemica et Biophysica Acta* 875 (1986), pp. 183-194.
Matz et al, "Micellar Complexes of Human Apolipoprotein A-I with Phosphatidylcholine and Cholesterol Prepared from Cholate-Lipid Dispersions," *J. Biological Chemistry*, vol. 257, No. 8, Apr. 25, 1982, pp. 4535-4540.
Matz et al, "Reaction of Human Lecithin Cholesterol Acyltransferase with Synthetic Micellar Complexes of Apolipoprotein A-I, Phosphatidycholine, and Cholesterol," *J. Biological Chemistry*, vol. 257, No. 8, Apr. 25, 1982, pp. 4541-4546.

*Primary Examiner*—Jeffrey E. Russel
*Attorney, Agent, or Firm*—Felfe & Lynch

[57] ABSTRACT

A reconstituted high density lipoprotein containing particle is disclosed. The particle is useful in removing excess lipid soluble material from a subject to which it is administered, as well as in delivery of lipid soluble pharmaceuticals to subjects or patients.

7 Claims, 1 Drawing Sheet

RECONSTITUTED HDL PARTICLES AND USES THEREOF

This application is a divisional of U.S. Ser. No. 052,489, filed May 20, 1987, now abandoned.

FIELD OF THE INVENTION

This invention relates to high density lipoprotein (HDL) associated apolipoprotein containing reconstituted particles, and use of these in removing lipid soluble materials from cells, body fluids, and the like. Of particular interest are reconstituted or synthetic HDL particles which are useful in treatment of hypercholestemia.

BACKGROUND AND PRIOR ART

Normal serum contains a number of lipoprotein particles which are characterized according to their density, namely, chylomicrons, VLDL, LDL and HDL. They are composed of free and esterified cholesterol, triglycerides, phospholipids, several other minor lipid components, and protein. Low density lipoprotein (LDL) transports lipid soluble materials to the cells in the body, while high density lipoprotein (HDL) transports these materials to the liver for elimination. Normally, these lipoproteins are in balance, ensuring proper delivery and removal of lipid soluble materials. Abnormally low HDL can cause a number of diseased states as well as constitute a secondary complication in others.

Under normal conditions, a natural HDL particle is a solid with its surface covered by a phospholipid bilayer that encloses a hydrophobic core. Apolipoprotein A-I and A-II attach to the surface by interaction of the hydrophobic face of their alpha helical domains. In its nascent or newly secreted form the particle is disk-shaped and accepts free cholesterol into its bilayer. Cholesterol is esterified by the action of lecithin:cholesterol acyltransferase (LCAT) and is moved into the center of the disk. The movement of cholesterol ester to the center is the result of space limitations within the bilayer. The HDL particle "inflates" to a spheroidal particle as more and more cholesterol is esterified and moved to the center. Cholesterol ester and other water insoluble lipids which collect in the "inflated core" of the HDL are then cleared by the liver.

Jonas, et al., *Meth. Enzym.* 128A: 553–582 (1986) have produced a wide variety of reconstituted particles resembling HDL. The technique involves the isolation and delipidation of HDL by standard methods (Hatch, et al., *Adv. Lip. Res.* 6: 1-68 (1968); 576-588 (1971)) to obtain apo-HDL proteins. The apoplipoproteins are fractionated and reconstituted with phospholipid and with or without cholesterol using detergent dialysis.

Matz, et al., *J. Biol. Chem* 257(8): 4535-4540 (1982) describe a micelle of phosphatidylcholine, with apolipoprotein Al. Various ratios of the two components are described, and it is suggested that the described method can be used to make other micelles. It is suggested as well to use the micelles as an enzyme substrate, or as a model for the HDL molecule. This paper does not, however discuss application of the micelles to cholesterol removal, nor does it give any suggestions as to diagnostic or therapeutic use.

Williams, et al., *Biochem & Biophys. Acta* 875: 183–194 (1986) teach phospholipid liposomes introduced to plasma which pick up apolipoproteins and cholesterol. Liposomes are disclosed, which pick up apolipoprotein in vivo, as well as cholesterol, and it is suggested that the uptake of cholesterol is enhanced in phospholipid liposomes which have interacted with, and picked up apolipoproteins.

Williams, et al., *Persp. Biol. & Med.* 27(3): 417–431 (1984) discuss lecithin liposomes as removing cholesterol. The paper summarizes earlier work showing that liposomes which contain apolipoproteins remove cholesterol from cells in vitro more effectively than liposomes which do not contain it. They do not discuss in vivo use of apolipoprotein containing liposomes or micelles, and counsel caution in any in vivo work with liposomes.

It is important to note that there is a clear and significant difference between the particles of the present invention, and the liposomes and micelles described in the prior art. The latter involve a bilayer structure of lipid containing molecules, surrounding an internal space. The construction of liposomes and micelles precludes filling the internal space, however, and any molecular uptake is limited to the space defined between the two lipid layers. As a result, there is much less volume available for pick up and discharge of materials such as cholesterol and other lipid soluble materials than there is for the particles of this invention, which expand in a fashion similar to a balloon, with interior space filling with the material of choice.

The present invention involves the production of reconstituted particles with and without free cholesterol in the bilayer using detergent dialysis These particles appear when viewed by negative staining transmission electron microscopy (TEM) as discoidal and are transformed to spheroidal particles upon exposure to LCAT. They retain their ability to act as substrates for LCAT and are transformed to spheroidal particles in a fashion similar to natural HDL. When reconstituted particles containing 10 percent mole fraction of tritiated cholesterol in the bilayer are exposed to LCAT for 12 hours, almost complete conversion of free cholesterol to cholesterol ester is achieved as determined by thin layer chromatography (TLC).

In summary, synthetic HDL particles are structural and functional analogs of natural HDL particles in that they (1) resemble nascent HDL particles when visualized under negative staining TEM, (2) are substrates for LCAT and (3) function as cholesterol acceptors which deplete cholesterol and other lipid soluble toxins from cells, such as human cells.

DETAILED DESCRIPTION OF PREFERRED EMBODIMENTS

Example I

Figure 1:
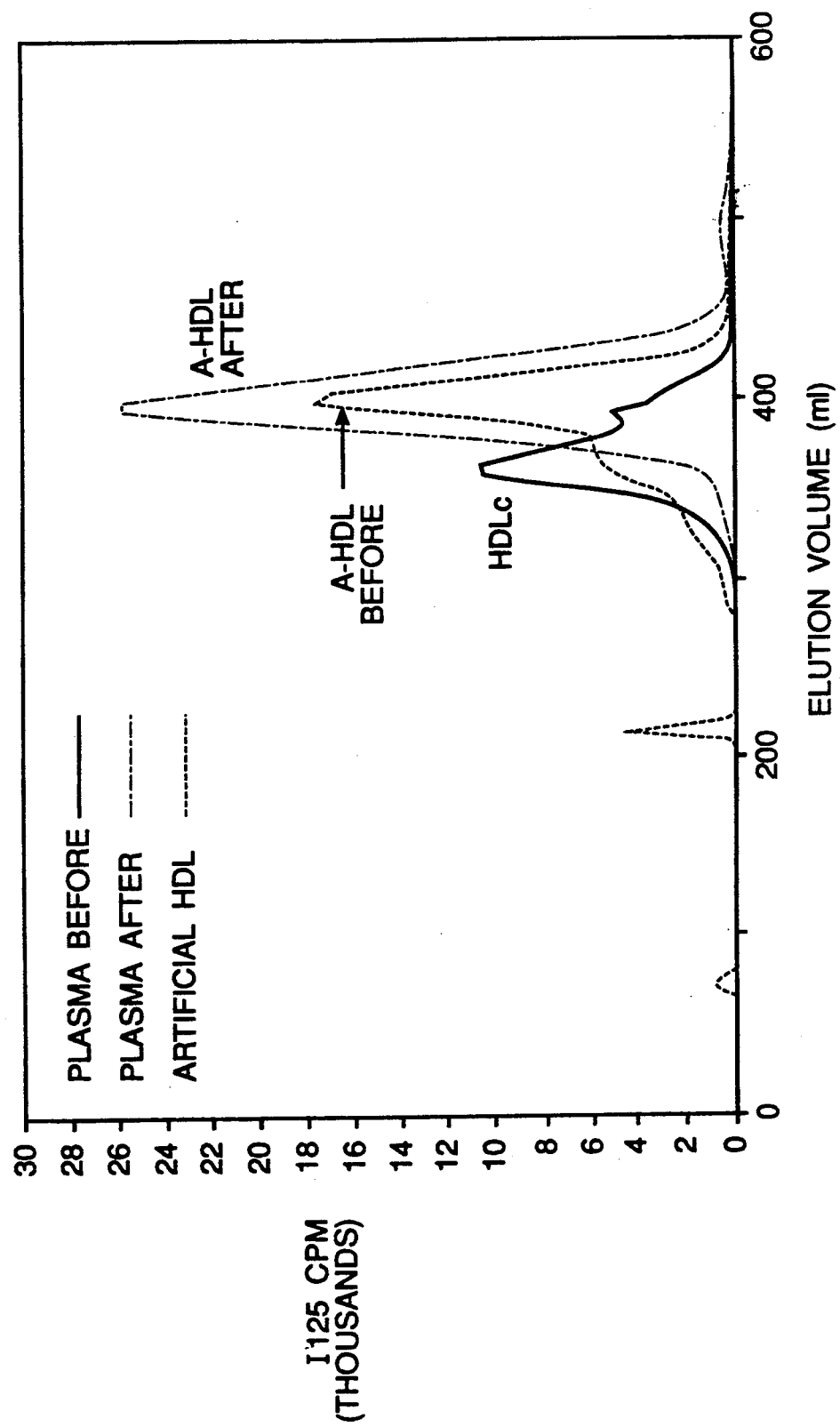
FIG. 1 depicts results obtained when rabbits were injected with the synthetic particles of the invention, and the HDL phospholipid content of the rabbits' plasma was assayed.

LDLs and HDLs were isolated via a series of ultracentrifugation steps. Procedures set out in, e.g., Scanu, et al. *Anal. Biochem* 44: 576-588 (1971); and Osborne in Segrest, et al. (eds) *Meth. Enzym.* 128(A); 213-222 (1986) were followed.

20mls (52 grams) of plasma was used per cenrifuge tube. These samples were then spun at $4.0 \times 10^4$ RPM for 20 hours at a plasma density of 1.006. This first centrifugation resulted in separation of floated chylomicrons and VLDLs (top 3-4 mls) of each tube. This material was discarded.

The remaining plasma was then pooled into a graduated cylinder, and its density raised to 1.063 by addition of 0.0768 g NaBr/ml of plasma, with complete dissolving of the NaBr. 20 mls (54g) of the dense plasma were distributed per centrifuge tube, and this was centrifuged at $4.0 \times 10^4$ RPM for 20 hours. LDLs were present in the top 3-4 mls of each sample, and this was removed and dialyzed against TRIS-EDTA buffer (pH 8.0) as described by Hatch, et al., *Adv. Lip. Res.* 6: 1-68 (1968) overnight at below room temperatures ($3 \times 1$ liter).

Once the LDLs were removed, the plasma was again pooled and its density raised to 1.2 by adding 0.213g of NaBr/ml of plasma. Again, 20 mls (56g) were placed in tubes, and centrifuged at $4.0 \times 10^4$ RPM for 40 hours. Floated HDLs were present in the top 3-4 mls of each tube. The HDLs were dialyzed in the same manner as the LDLs, with the clear middle zone reserved for LCAT isolation and purification.

Once this step was performed, the HDLs were solvent extracted. In this procedure, the HDL-containing solutions were dialyzed against ammonium carbonate buffer (0.01, i.e., 1.572g/ml), overnight at 10° C., followed by shell-freezing (10 mg HDL samples), followed by lyophilization.

In a second step, the lyophilized HDL was extracted using ethyl alcohol:ether in a 3:1 (V/V) ratio. The EtOH:ether mixture was chilled to 0° C., and 50 mls were used per 10 mg HDL. These were mixed and stored at 0° C. for 30 minutes, followed by centrifugation ($9 \times 10^3$ RPM) for 10 minutes, at 0° C. Supernatant was discarded, and this second step was repeated two more times.

The samples remaining were then extracted in diethyl ether for 30 minutes, and centrifuged as described supra. This step is repeated two more times, and the final supernatant was aspirated off and dried under a stream of nitrogen.

The apolipoprotein or apo HDL which was obtained was then tested for residual phospholipids and cholesterol.

Example II

Making Reconstituted HDL Particles

A. Rehydration of Apo-HDL 7.2 mg of Apolipoprotein containing HDL (5.02 mg are Apolipoprotein AI and Apolipoprotein AII) were dissolved in 1 ml TRIS-EDTA containing 3M guanidine HCl (0.287 g/ml) at pH 8.0 in a $12 \times 75$ mm test tube capped with paraffin. This was placed in a rotating shaker and allowed to dissolve for a minimum of one hour. If necessary, sonication was used to disperse the protein.

The resulting solution was dialyzed against 2 liters of TRIS-EDTA buffer (10 mM NaCl, 10 mM EDTA, 1mM azide; pH 8.0), at below room temperature. The tubing used in the dialysis has a MW cutoff of 12,000. This is because Apo AI and AII constitute 70% of Apo HDL, and 30% more protein was used to take into consideration the loss of proteins with molecular weight less than 12,000. A dialysis tube which will not lose proteins of this size is therefore necessary.

B. Preparing lipid:cholate and protein:cholate dispersion

To make particles without cholesterol, 14.2 mg of egg phosphatidylcholine (EPC) was weighed out into a tared, $13 \times 100$ mm test tube, with addition of 1 ml chloroform to dissolve it completely. This was dried to a thin film under $N_2$.

To make particles with cholesterol, 12.74 mg of EPC was weighed and dissolved as described supra, and 69.6 ul of a 10 mg/ml stock solution of cholesterol in chloroform was added. Drying was as above.

Whether cholesterol containing or cholesterol free films were prepared, 3 mls of 18mM sodium cholate was added to the film containing tubes. The tubes were sealed and sonicated for about 1 minute until all of the lipid was dispersed.

The apolipoprotein solution prepared as described supra was transferred to a 15 ml Falcon tube, and spun to pellet undissolved material. The apolipoprotein solution was transferred to a disposable test tube ($13 \times 100$ mm; 1 ml of solution), and 1 ml of 36 mM sodium cholate was added. The final concentration of cholate in this apolipoprotein:cholate solution was 18 mM.

C. Preparing Reconstituted HDL Particles

The lipid cholate solution was added to the protein cholate solution, and the tube containing these was sealed, swirled gently, and incubated overnight at 10° C.

The sample was then dialyzed against 3, 2 liter changes of TRIS-EDTA, at 10° C. It is important that the sample remain at 10° C. through the entire dialysis procedure. As described supra, the same conditions are in force regarding dialysis tubing.

This procedure produced reconstituted particles which were transferred to a 15 ml Falcon tube and centrifuged to remove large materials. Reconstituted HDL particles remained in the supernatant and could be filter sterilized, e.g., using a 0.22 um syringe filter.

Example III

The Use of Synthetic HDL to remove Cholesterol from Cells

The ability of cholesterol-free synthetic HDL particles to remove cholesterol from cholesterol-loaded human peripheral blood monocyte-derived macrophages was determined. Macrophages were grown in delipidated heat-treated human serum (DHS) for two days to up-regulate the LDL receptors. The cells were fed LDL and acetylated LDL for two days to load the cells with cholesterol. The LDL was removed and the cells were rinsed with DHS. The cells were incubated in DHS containing approximately 10 mg/ml LCAT and 0.1 mg/ml (protein) reconstituted HDL particles for four hours. After loading, cells appeared to contain large oil droplets and after a four hour incubation period, they appeared to be almost completely depleted of these droplets. Two replicated experiments were conducted. The synthetic HDL particles acquired 46 and 62 ug/ml cholesterol, respectively.

Example IV

Demonstration that Injected Synthetic HDL Particles can Increase Plasma HDL Concentrations In Vivo The effect of injected synthetic HDL particles on plasma HDL concentration in the heterozygous Watanabe Heritable Hyperlipidemic Rabbit (WHHL) was determined. Rabbit HDL was purified from normal rabbit plasma and used directly (natural HDL) or used to produce HDL apolipoproteins which in turn were combined with egg phospholipid to make synthetic HDL as described above in Example II. Three male 3 kg heterozygous WHHL rabbits were randomly assigned to one of the following experimental treatments: (1) a saline control, (2) a synthetic HDL or (3) a natural HDL treatment. The saline control animal received a single injection of 20 ml of sterile normal saline. The synthetic HDL and natural HDL treatment animals received 100 mg of synthetic or natural HDL (measured as phospholipid) injected in 20 ml of saline. HDL phospholipid was measured 30 to 60 minutes after injection. Table 1 shows the observed changes in HDL phospholipid assuming that, after injection the synthetic HDL behaves as natural HDL.

TABLE 1

Observed changes from baseline in HDL phospholipid (mg/dl) after injection of saline, natural or synthetic HDL.

|  | Saline | Natural HDL | Synthetic HDL |
| --- | --- | --- | --- |
| Baseline | 78.0 | 78.0 | 53.2 |
| Post 30 Min | — | 100.4 | 78.0 |
| Post 60 Min | 83.6 | 97.6 | 72.8 |

Example V

Demonstration that Injected Synthetic HDL is Accepted as Natural HDL in Animals

This study demonstrated that injected synthetic HDL particles are accepted as natural HDL in animals. Rabbit HDL was purified from normal rabbit plasma and used directly (natural HDL) or used to produce HDL apolipoproteins which in turn were combined with egg phospholipid to make synthetic HDL as described above in Example II. Three male 3 kg heterozygous WHHL rabbits were given an injection of saline, synthetic or natural HDL. The saline control animal received an injection of 20 ml of sterile normal saline. The synthetic and natural HDL treatment animals received 100 mg of synthetic or natural HDL (measured as phospholipid) injected in 20 ml of saline. Blood was drawn from each animal at 30 and 60 minutes after injection. A 1 ml aliquot of whole plasma from each sample was passed down a rabbit anti-LDL sepharose column (sheep anti-rabbit LDL covalently linked to Sepharose CL-4B) to remove beta lipoproteins. The plasma eluting from the columns was essentially all HDL. The columns were washed with three additional mls of saline. HDL cholesterol was measured by the standard enzymatic cholesterol assay.

Table 2 shows the observed changes in HDL cholesterol assuming that after injection the synthetic HDL behaves as natural HDL. HDL cholesterol quadrupled in the animal that received natural HDL and almost doubled in the animal receiving synthetic HDL. The difference in response between natural versus synthetic particles is due to the fact that the natural HDL injection contained natural cholesterol-filled particles, whereas the synthetic particles were completely devoid of cholesterol and were in the process of filling when the measurements were taken. The assay used specifically measures the cholesterol content.

TABLE 2

Observed changes from baseline in HDL cholesterol (mg/dl) after injection of saline, natural or synthetic HDL.

|  | Saline | Natural HDL | Synthetic HDL |
| --- | --- | --- | --- |
| Baseline | 24.9 | 10.3 | 12.4 |
| Post 30 Min | 23.0 | 43.7 | 22.9 |
| Post 60 Min | 23.7 | 43.7 | 22.9 |

Example VI

Demonstration that Injected Synthetic HDL Converts Natural HDLc to HDL2 in Animals This study demonstrated that synthetic HDL converts mature cholesterol-rich HDL to a smaller particle that can accept additional cholesterol and resembles HDL2 in animals. Rabbit HDL was purified from normal rabbit plasma and used directly (natural HDL) or used to produce HDL apolipoproteins which in turn were combined with egg phospholipid to make synthetic HDL as described above in Example II. Two male 3 kg heterozygous WHHL rabbits were given an injection of either synthetic or natural HDL. The synthetic and natural HDL treatments received 100 mg of 125 I-labelled synthetic or unlabeled natural HDL (measured as phospholipid) injected in 20 ml of saline. Blood was drawn from each animal at 30 and 60 minutes after injection. Whole plasma from the 30 and 60 minute samples from each animal were pooled, the natural HDL sample was spiked with 125 I-labeled synthetic HDL particles and 3 mls of each sample were run on $25 \times 100$ cm agarose A 0.5M columns. In addition, a sample of synthetic HDL particles was spiked with a small volume of 125 I-labeled synthetic particles and run on a column. FIG. 1 shows the elution profile of counts per minute as a function of elution volume in mls. The majority of HDL in plasma occurs as large cholesterol-rich particle known as HDLc which elutes in approximately 380 mls. The synthetic HDL is a smaller particle which behaves like human HDL2, eluting in approximately 400 mls. HDL2 is generally considered to be the anti-atherogenic HDL. This demonstrates the conversion of the plasma in the animal from the mature cholesterol rich form of HDLc to a form which can accept additional cholesterol and which resembles HDL2.

The synthetic HDL particles described herein will be seen by those skilled in the art to be useful in various biological and biochemical application. It has long been known that liposomes, e.g., are useful in drug delivery systems. (See, e.g., Fountain, et al., U.S. Pat. No. 4,610,868; Ryan, et al., U.S. Pat. No. 4,544,545; Ash, et al., U.S. Pat. No. 4,448,765; and Kelly, U.S. Pat. No. 4,551,288, as some examples of the literature on this point). As has been pointed out supra, however, liposomes have extremely limited capacity for carrying any substance. The reconstituted particles of this invention, due to their carrying capacity, represent a substantial improvement over liposomes and micelles as used in drug delivery.

Additionally, the particles described therein will be seen to be useful in removing lipid soluble wastes including, but not limited to, cholesterol, cholesterol esters, endotoxins, insecticides such as DDT, and carcinogens such as dioxin. In each case, the particles supplement HDL levels in a subject to which they are administered, and act to transport organic or inorganic lipophilic substances to the liver, which is the site of lipid soluble waste excretion.

Typical diseases which can be treated by administration of these particles include, but are not limited to, coronary atherosclerosis, and hyperlipidemia resulting from, e.g., diabetes and nephrotic diseases.

In each case, treatment will vary because each subject will differ and require different amounts of particles. As HDLs occur normally in biological systems and are processed rather quickly, they are non-toxic and problems associated with, e.g., "LD" determinations for new pharmaceuticals are not an issue. Intravenous administration is the accepted mode of delivery.

Another application of the invention is in separation of harmful substances from body fluids which contain excess or harmful lipids. In this application, synthetic HDL particles are linked to an inert carrier such as, but not limited to, sepharose columns or other stationary supports. The linkage is accomplished by any of the known materials which are used to attach substances to carriers, such as cyanogen bromide. Via appropriate catheters, tubing, etc., body fluids are removed and passed over the inert column with attached synthetic particles, for a time sufficient for the HDL particles to pick up and remove the lipid materials. In this way, toxic lipid soluble substances such as dioxin, or lipid materials which are present in fluids, such as excess blood cholesterol, are removed. In the case of cholesterol, synthetic HDL particle containing columns are used "in line" with LDL-pheresis columns used in connection therewith. In this situation the HDL column cleanses naturally occurring HDL of cholesterol and returns the ability of natural HDL as a cholesterol carrier thereto.

The HDL particles function, as described supra, as delivery vehicles for drugs. One key example is the delivery of pharmaceutically active phospholipids, or other drugs which can be attached to the lipid or protein portion of the particle either before, during, or after particle formation. One example is a particle in which is incorporated a bifunctional reagent which inserts one end into the polar head portion of the particle phospholipid, with a site for drug attachment at the other functional moiety.

Additionally, the synthetic HDL particles described herein will be seen by those skilled in the art to be effective in various diagnostic procedures. As synthetic HDL particles can have a hydrophobic core, various determinable substances, or "tags", such as chromogenic, chromophoric, fluorogenic and other labelled reagents can be incorporated therein in order to measure activity of lipid active factors in the plasma of a patient. HDL particles constructed without hydrophobic cores accept lipid in the manner described supra, from subject plasma, and the lipid donating potential of the subject's plasma quantitatively measured as the amount of chromogen accepting capacity of synthetic HDL particles following "inflation" or "filling" with plasma lipid. Examples, but not limits, on the lipid active factors measurable thereby are lecithin cholesterol acetyltransferase (LCAT); cholesterol ester transfer protein (CET); cellular HDL receptor activity; plasma cholesterol transport potential; and removal of biotoxins. The last of these is performed in vitro such as is described supra. Each of these examples involve mechanisms which the art views as involved in cholesterol ester (nonpolar lipid) transport, and atherosclerosis. In situations where chromogens are used, these are screened for their ability to partition into the hydropholic care of inflated synthetic particles after reaction with LCAT in the presence of a cholesterol donor. Acceptable chromogens include those which can be spectrophotometrically measured at from 300 to 500 nM.

While there have been described what are at present considered to be preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Method for treating a subject for endotoxin caused toxicity comprising administering to said subject an amount of a reconstituted, cholesterol free particle which contains (i) an HDL associated apolipoprotein and (ii) a lipid in which the endotoxin causing said toxicity is soluble sufficient to alleviate toxicity caused by said endotoxin.

2. Method for treating a subject for endotoxin caused toxicity comprising administering to said subject an amount of a reconstituted particle containing (i) cholesterol, (ii) an HDL associated apolipoprotein, and (iii) a lipid in which endotoxin causing said toxicity is soluble, in an amount sufficient to alleviate toxicity caused by said endotoxin.

3. Method of claim 1, wherein said reconstituted particle consists of said high density lipoprotein associated apolipoprotein associated apolipoprotein is apolipoprotein AI.

4. Method of claim 1, wherein said high density lipoprotein associated apolipoprotein is apolipoprotein AII.

5. Method of claim 1, wherein said high density lipoprotein associated apolipoprotein is apolipoprotein AIII.

6. Method of claim 2, wherein said high density lipoprotein associated apolipoprotein is apolipoprotein AI.

7. Method of claim 2, wherein said high density lipoprotein associated apolipoprotein is apolipoprotein AII.

* * * * *

UNITED STATES PATENT AND TRADEMARK OFFICE
CERTIFICATE OF CORRECTION

PATENT NO. : 5,128,318

DATED : July 7, 1992

INVENTOR(S) : Daniel M. Levine et al.

It is certified that error appears in the above-identified patent and that said Letters Patent is hereby corrected as shown below:

Column 1, line 51: after "(1968)" insert -- Scanu et al., Anal. Biochem. 44: --.

Column 3, line 35: change "103" to -- $10^3$ --.

Claim 3, lines 3-4 (column 8, lines 44-45): delete "associated apolipoprotein is apolipoprotein AI" and replace by -- and said lipid in which said endotoxin is soluble --.

Claim 4, line 2 (column 8, line 48): change "AII" to -- AI --.

Signed and Sealed this

Twenty-fifth Day of January, 1994

Attest:

BRUCE LEHMAN

*Attesting Officer*   *Commissioner of Patents and Trademarks*